US012201024B2

(12) United States Patent
Da Cruz et al.

(10) Patent No.: US 12,201,024 B2
(45) Date of Patent: Jan. 14, 2025

(54) METHODS FOR FORMING AN INVASIVE DEPLOYABLE TRANSDUCER USING SHAPE MEMORY POLYMER

(71) Applicant: GE Precision Healthcare LLC, Milwaukee, WI (US)

(72) Inventors: Edouard Da Cruz, Nice (FR); Giandonato Stallone, Nice (FR); Flavien Daloz, Antibes (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 597 days.

(21) Appl. No.: 15/930,290

(22) Filed: May 12, 2020

(65) Prior Publication Data

US 2021/0353319 A1 Nov. 18, 2021

(51) Int. Cl.
| | | |
|---|---|---|
| *A61B 8/00* | (2006.01) | |
| *H01R 4/01* | (2006.01) | |
| *H10N 30/00* | (2023.01) | |
| *H10N 30/071* | (2023.01) | |
| *H10N 30/072* | (2023.01) | |

(Continued)

(52) U.S. Cl.
CPC .............. *H10N 30/071* (2023.02); *H01R 4/01* (2013.01); *H10N 30/072* (2023.02); *H10N 30/088* (2023.02); *H10N 30/875* (2023.02); *H10N 30/88* (2023.02); *A61B 8/44* (2013.01); *A61B 8/4444* (2013.01); *A61B 8/4483* (2013.01); *A61B 8/4494* (2013.01); *B06B 1/0607* (2013.01)

(58) Field of Classification Search
CPC ............... H01L 41/311; H01L 41/0475; H01L 41/053; H01L 41/312; H01L 41/338; H01R 4/01; A61B 8/44; A61B 8/4444; A61B 8/4483; A61B 8/4494; A61B 8/0883; A61B 8/085; A61B 8/12; A61B 8/4488; B06B 1/0607
See application file for complete search history.

(56) References Cited

U.S. PATENT DOCUMENTS 5,680,863 A * 10/1997 Hossack ................ G10K 11/32
600/459
7,220,233 B2 5/2007 Nita et al.
(Continued)

FOREIGN PATENT DOCUMENTS

| GB | 2590475 B | 2/2022 |
|---|---|---|
| JP | 5709366 B2 | 4/2015 |

OTHER PUBLICATIONS

Kaojin Wang, Yong-Guang Jia, Chuanzhuang Zhao, X.X. Zhu, Multiple and two-way reversible shape memory polymers: Design strategies and applications, Progress in Materials Science, vol. 105, 2019, 100572 https://doi.org/10.1016/j.pmatsci.2019.100572. (Year: 2019).*

(Continued)

*Primary Examiner* — Joel Lamprecht
*Assistant Examiner* — James F Mcdonald, III
(74) *Attorney, Agent, or Firm* — McCoy Russell LLP

(57) ABSTRACT

Various methods and systems are provided for a transducer for a deployable catheter. In one example, a method for forming the transducer includes coupling an acoustic stack to a shape memory material while in a planar configuration to form a transducer and exposing the shape memory material to a curling stimulus to adjust the transducer to a curved configuration.

17 Claims, 11 Drawing Sheets

(51) Int. Cl.
*H10N 30/088* (2023.01)
*H10N 30/87* (2023.01)
*H10N 30/88* (2023.01)
*B06B 1/06* (2006.01)

(56) References Cited

U.S. PATENT DOCUMENTS

| | | |
|---|---|---|
| 7,500,954 B2 | 3/2009 | Wilser et al. |
| 10,405,830 B2 | 9/2019 | Garbini et al. |
| 2007/0066902 A1 | 3/2007 | Wilser |
| 2008/0146937 A1 | 6/2008 | Lee et al. |
| 2017/0086974 A1* | 3/2017 | Lashinski ............ A61B 8/0883 |
| 2019/0142528 A1* | 5/2019 | Vertikov ................ A61B 34/20 |
| | | 600/424 |
| 2019/0223835 A1* | 7/2019 | Seyed-Bolorforosh ...................... |
| | | A61B 8/445 |

OTHER PUBLICATIONS

CN application 202110462229.7 filed Apr. 27, 2021—Office Action issued Apr. 1, 2024, 6 pages.

* cited by examiner

METHODS FOR FORMING AN INVASIVE DEPLOYABLE TRANSDUCER USING SHAPE MEMORY POLYMER

Embodiments of the subject matter disclosed herein relate to a transducer for a deployable catheter.

BACKGROUND

Invasive devices may be used to obtain information about tissues, organs, and other anatomical regions that may be difficult to gather via external scanning or imaging techniques. An invasive device may be a deployable catheter which may be inserted intravenously into a patient's body. In one example, the device may be used for intracardiac echocardiography imaging where the device is introduced into the heart via, for example, the aorta, inferior vena cava, or jugular vein. The device may include a transducer probe with a wide field of view (FOV) that allows that probe to obtain images in a three-dimensional environment.

BRIEF DESCRIPTION

In one embodiment, a method for forming a transducer comprises coupling an acoustic stack to a shape memory material while in a planar configuration to form the transducer and exposing the shape memory material to a curling stimulus to adjust the transducer to a curved configuration. The shape memory material may be exposed to a straightening stimulus prior to exposure to the curling stimulus to transition the shape memory material to the planar configuration. Thus, the transducer may be fabricated while in a planar geometry, allowing increased precision during manufacturing with respect to fabricating the transducer on a curved substrate. In this way, a radial transducer with a wide field of view for a deployable invasive device may be efficiently produced at low cost.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
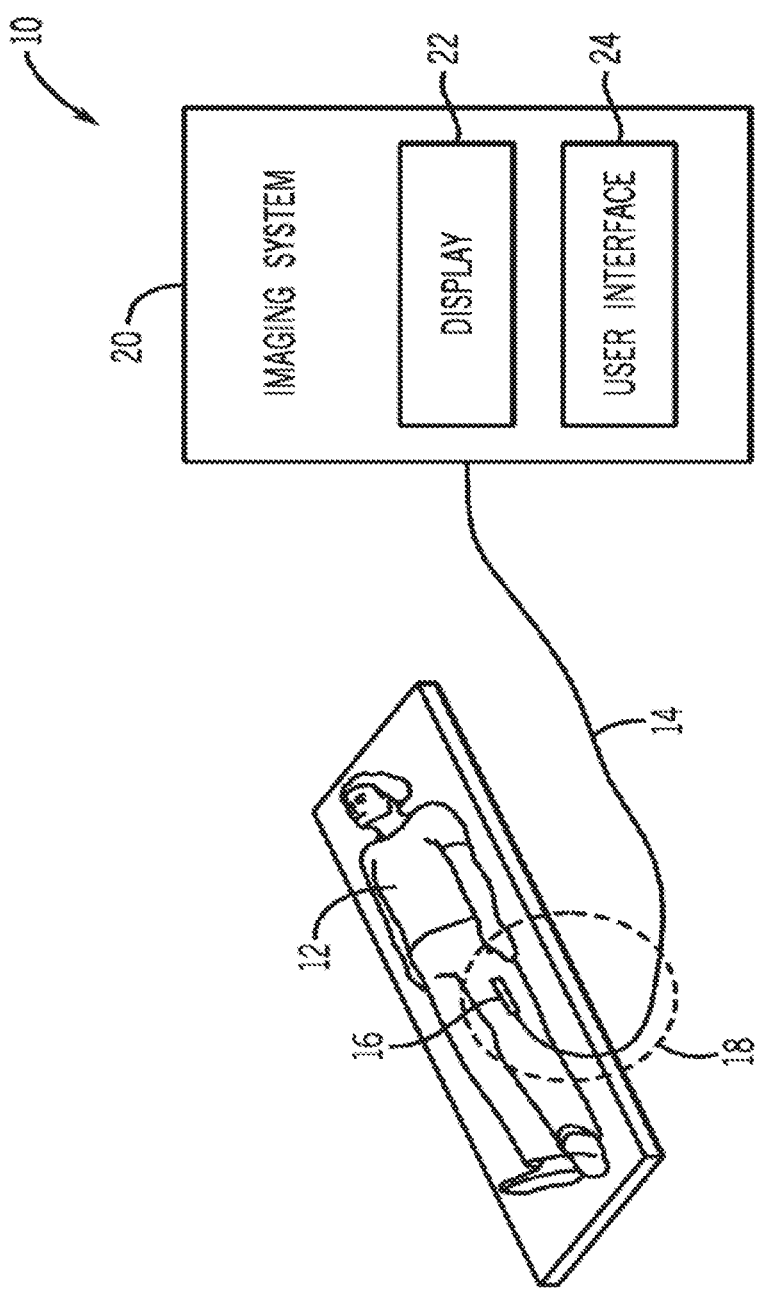
FIG. 1 shows a block diagram of an exemplary imaging system including a deployable catheter.
Figure 2:
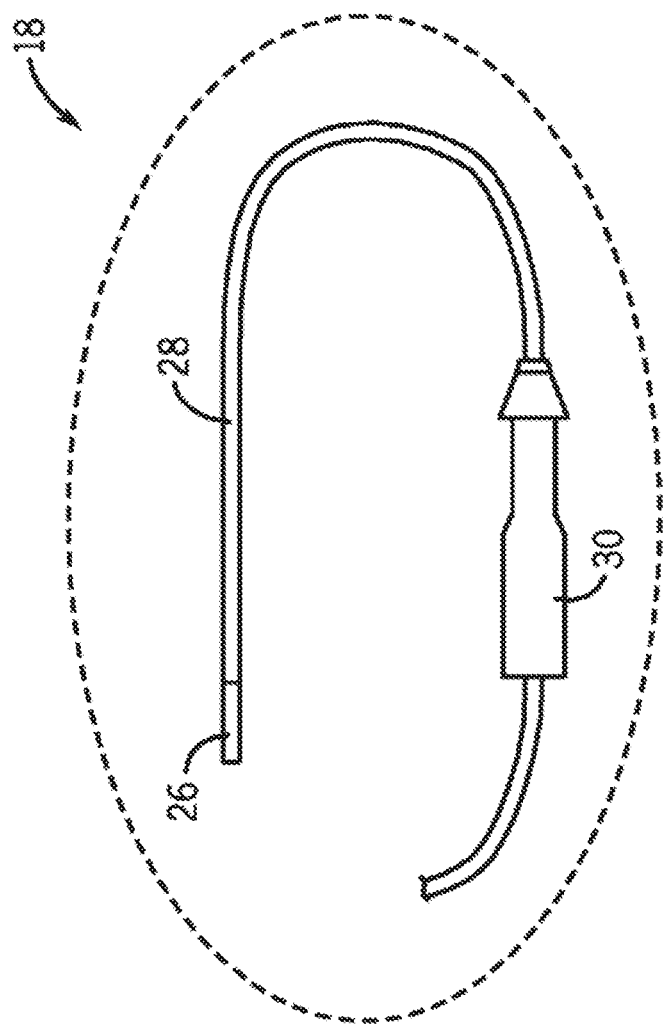
FIG. 2 shows the deployable catheter of FIG. 1 in greater detail, including an exemplary imaging catheter tip and transducer for use in the system illustrated in FIG. 1.
Figure 3:
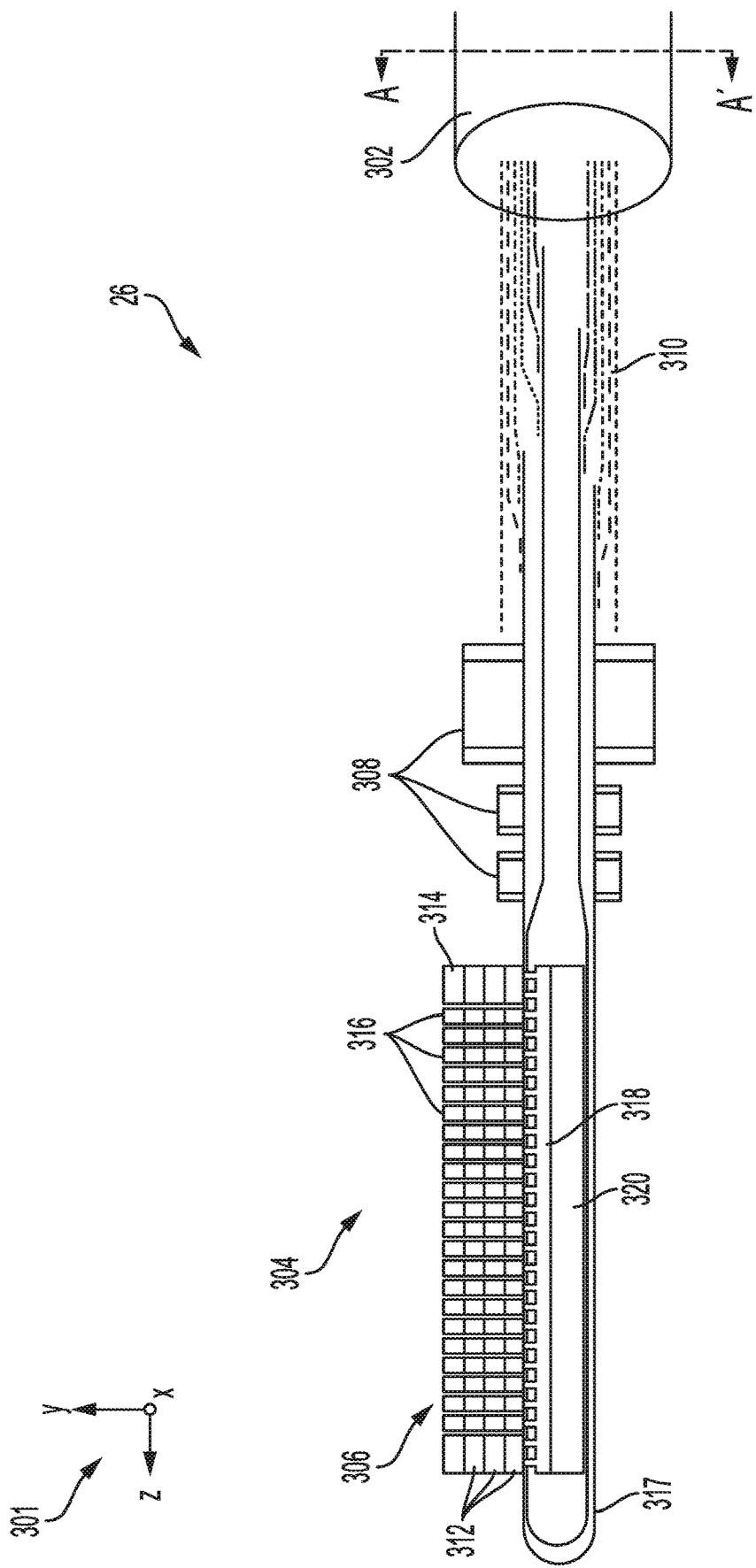
FIG. 3 shows inner components of the exemplary imaging catheter tip which may be included in the deployable catheter of FIG. 2.
Figure 5:
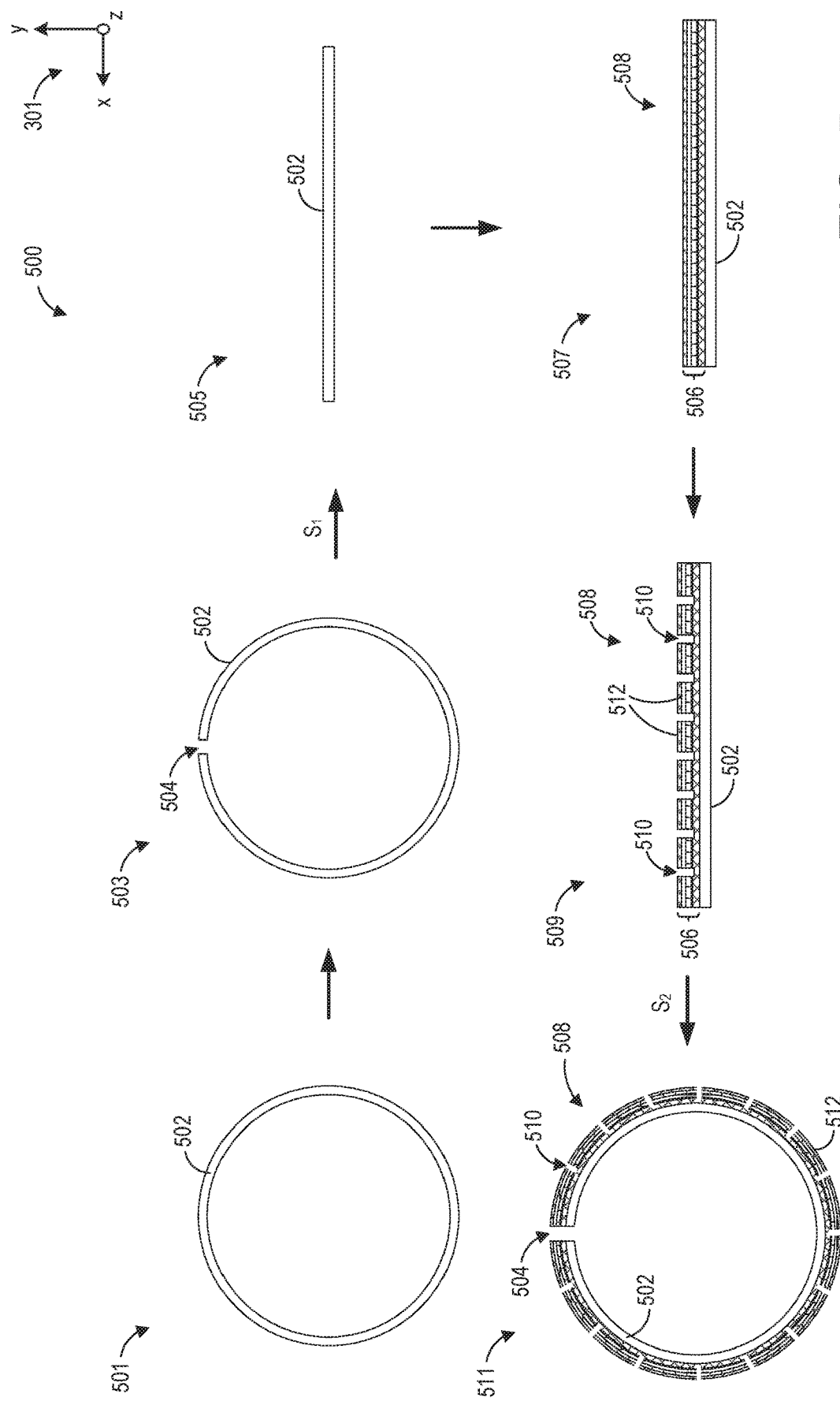
FIG. 5 is a first diagram showing a process for fabricating a radial transducer adapted with a shape memory material and configured to be implemented in a deployable catheter.
Figure 7:
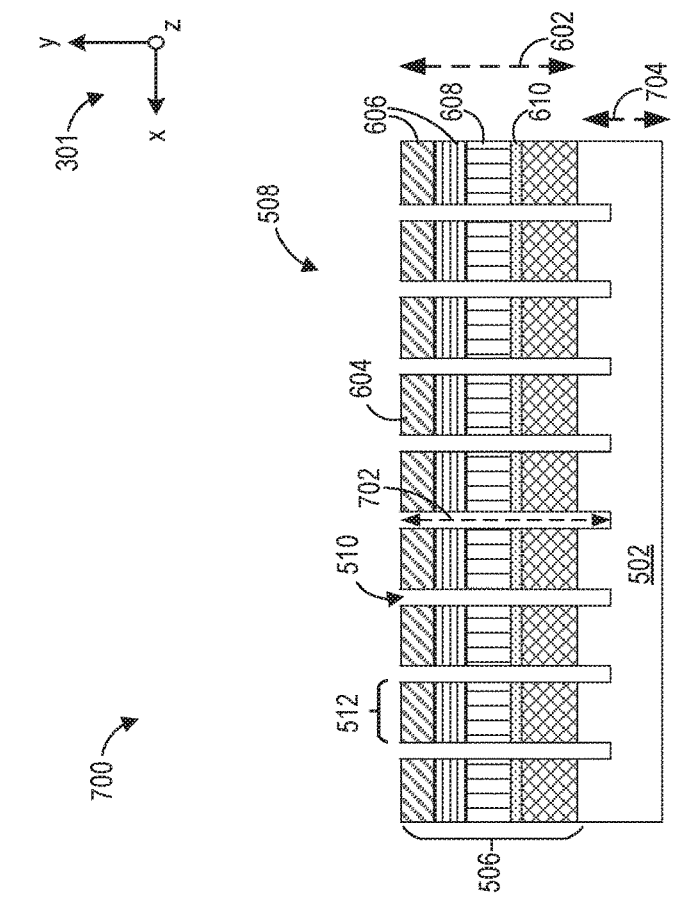
FIG. 7 shows a second example of how a transducer adapted with a shape memory material may be diced.
Figure 6:
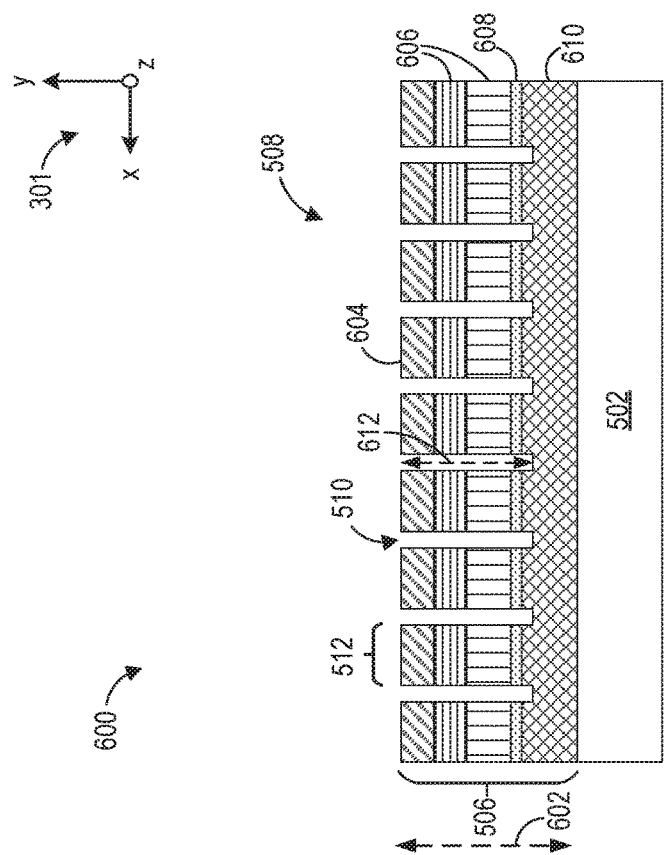
FIG. 6 shows a first example of how a transducer adapted with a shape memory material may be diced.
Figure 8:
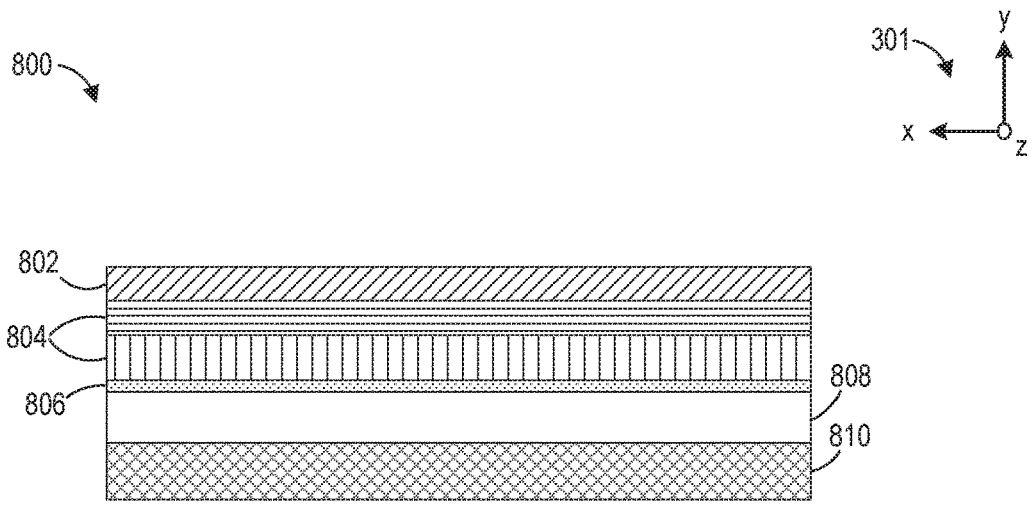
FIG. 8 shows a first arrangement of layers of a transducer adapted with a shape memory material.
Figure 9:
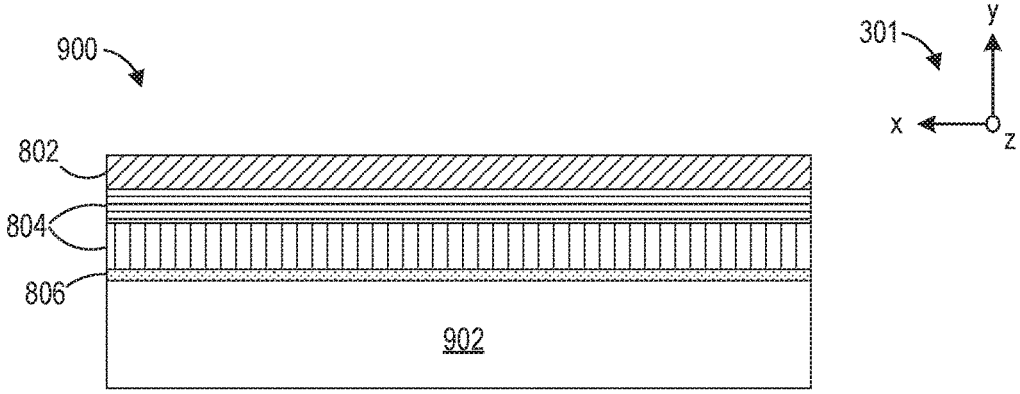
FIG. 9 shows a second arrangement of layers of a transducer adapted with a shape memory material.
Figure 10:
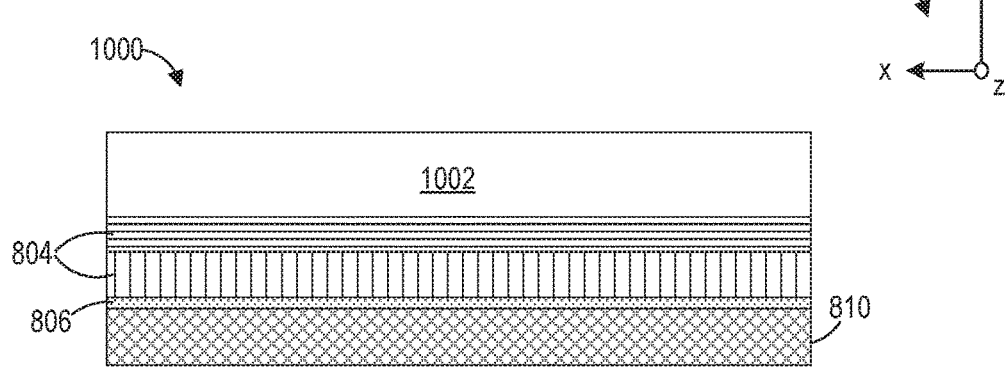
FIG. 10 shows a third arrangement of layers of a transducer adapted with a shape memory material.
Figure 12:
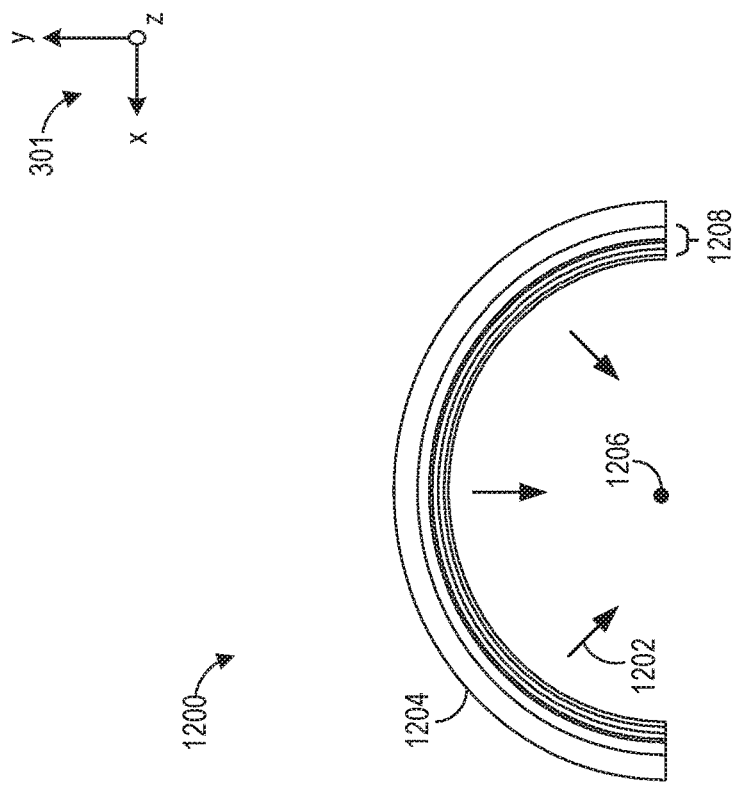
FIG. 12 shows an example of a concave radial transducer adapted with a shape memory material.
Figure 11:
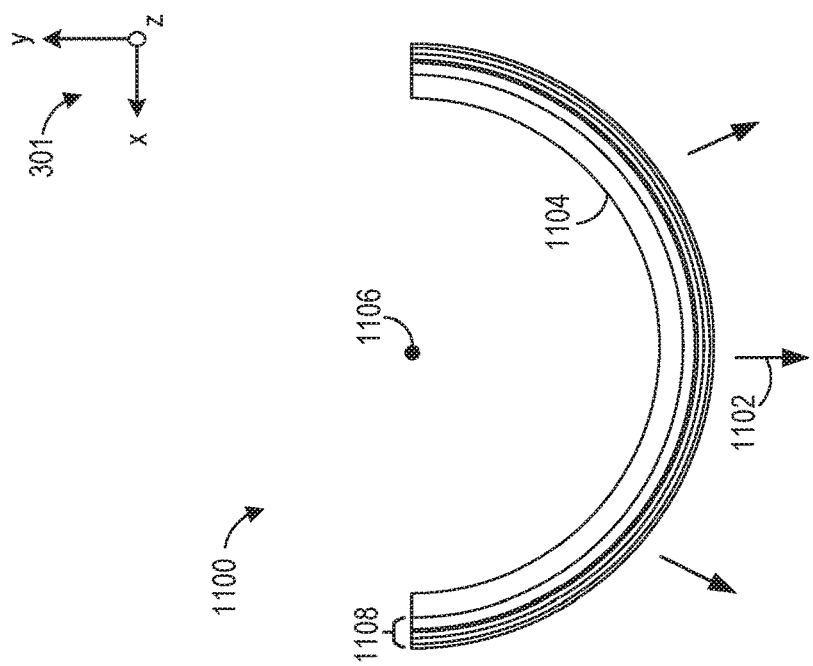
FIG. 11 shows an example of a convex radial transducer adapted with a shape memory material.

The following description relates to various embodiments of a deployable invasive device, such as a deployable catheter. The deployable catheter may be included in an imaging system to be inserted into a patient to obtain information about internal tissues and organs. An example of an imaging system equipped with a deployable catheter is shown in FIG. 1. A side view of the deployable catheter is depicted in FIG. 2 and inner components of the deployable catheter are illustrated in FIG. 3. A cross-sectional view of the deployable catheter is shown as a schematic in FIG. 4. The deployable catheter may include a radial transducer adapted with a shape memory material. The shape memory material may enable the transducer to transition between a first shape and a second shape, as shown in FIG. 5 during a manufacturing process to fabricate the transducer. The manufacturing process is further described in FIG. 14 in an example of a method for forming the radial transducer. The manufacturing process may include cutting, e.g., dicing, of the transducer where the dicing may be precisely controlled as a result of adjustment of the transducer to a planar configuration via the shape memory material. Examples of how the transducer may be diced are shown in FIGS. 6 and 7 and further shown in FIG. 15 along with an alternate positioning of the shape memory material. The incorporation of the shape memory material into the transducer may also allow a positioning of the shape memory material within an acoustic stack of the transducer to be varied, as illustrated in FIGS. 8-10. The radial transducer may be implemented as a 360° field of view (FOV) transducer but may have alternate configurations in other examples, such as a convex transducer as depicted in FIG. 11 and a convex transducer as shown in FIG. 12. The manufacturing process may be further applied to non-radial transducers utilizing a shape memory material to adjust a footprint of the transducer, as shown in a second diagram in FIG. 13.

FIGS. 1-13 and 15 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Medical imaging techniques, such as endoscopic ultrasound imaging, may be used to obtain real-time data about a patient's tissues, organs, blood flow, etc. However, high resolution images providing a complete view of a three-dimensional environment, such as inner cavities of the tissues and organs, may be difficult to obtain using a transducer probe with a linear array. In such instances, a deployable catheter outfitted with a radial transducer probe may be inserted into the patient and directed to a target site. The radial transducer probe may have up to a 360° field of view (FOV), thereby providing a full visualization of a target anatomical region that may be easily interpreted by operators. The radial transducer probe may include a curved configuration of one or more transducer arrays of the probe. The curved configuration may include the one or more transducer arrays having a non-planar geometry, e.g., bent, semi-circular, circular, spiral, concave, convex, folded, etc.

The deployable catheter may have a small diameter to allow the catheter to pass intravenously through a patient. The radial transducer probe may thus have an outer diameter no greater than that demanded of the deployable catheter. Fabrication of transducers with small radii of curvature, however, may require complicated tooling and complex manipulation of transducer components. Furthermore, controlling a thickness of adhesives used to laminate components onto a curved substrate may be challenging. As a result, the fabrication process may be costly and time consuming.

In one example, the issues described above may be at least partially addressed by incorporating a shape memory material into the transducer of the deployable catheter. The shape memory material may be a shape memory polymer (SMP) configured to alternate between at least two different shapes. In this way, the SMP may be adjusted to a conformation that simplifies fabrication of the transducer and then returned to a geometry that allows the transducer to obtain high quality data when deployed in the patient.

Turning now to FIG. 1, a block diagram of an exemplary system 10 for use in medical imaging is illustrated. It will be appreciated that while described as an ultrasound imaging system herein, the system 10 is a non-limiting example of an imaging system which may utilize a deployable device to obtain medical images. Other examples may include incorporating other types of invasive probes such as endoscopes, laparoscopes, surgical probes, intracavity probes, amongst others. The system 10 may be configured to facilitate acquisition of ultrasound image data from a patient 12 via an imaging catheter 14. For example, the imaging catheter 14 may be configured to acquire ultrasound image data representative of a region of interest in the patient 12 such as the cardiac or pulmonary region. In one example, the imaging catheter 14 may be configured to function as an invasive probe. Reference numeral 16 is representative of a portion of the imaging catheter 14 disposed inside the patient 12, such as inserted into a vein. Reference numeral 18 is indicative of a portion of the imaging catheter 14 depicted in greater detail in FIG. 2.

The system 10 may also include an ultrasound imaging system 20 that is in operative association with the imaging catheter 14 and configured to facilitate acquisition of ultrasound image data. It should be noted that although the exemplary embodiments illustrated hereinafter are described in the context of a medical imaging system, such as an ultrasound imaging system, other imaging systems and applications are also contemplated (e.g., industrial applications, such as nondestructive testing, borescopes, and other applications where ultrasound imaging within confined spaces may be used). Further, the ultrasound imaging system 20 may be configured to display an image representative of a current position of the imaging catheter tip within the patient 12. As illustrated in FIG. 1, the ultrasound imaging system 20 may include a display area 22 and a user interface area 24. In some examples, the display area 22 of the ultrasound imaging system 20 may be configured to display a two- or three-dimensional image generated by the ultrasound imaging system 20 based on the image data acquired via the imaging catheter 14. For example, the display area 22 may be a suitable CRT or LCD display on which ultrasound images may be viewed. The user interface area 24 may include an operator interface device configured to aid the operator in identifying a region of interest to be imaged. The operator interface may include a keyboard, mouse, trackball, joystick, touch screen, or any other suitable interface device.

FIG. 2 illustrates an enlarged view of the portion 18 shown in FIG. 1 of the imaging catheter 14. As depicted in FIG. 2, the imaging catheter 14 may include a tip 26 on a distal end of a flexible shaft 28. The catheter tip 26 may house a transducer and motor assembly. The transducer may include one or more transducer arrays, each transducer array including one or more transducer elements. The imaging catheter 14 may also include a handle 30 configured to facilitate an operator manipulating the flexible shaft 28.

An example of the catheter tip 26 of FIG. 2 is shown in FIG. 3. A set of reference axes 301 are provided, indicating a y-axis, an x-axis, and a z-axis. The catheter tip 26 may have a housing 302 surrounding a transducer 304 which may include at least one transducer array 306, capacitors 308, and a catheter cable 310. In one example, the transducer 304 may be a radial transducer with a curved outer geometry. For example, a cross-section of the transducer, taken along the x-y plane, may be circular or semi-circular, or other curved configurations such as spiral, slighty curved, etc. The other components not shown in FIG. 3 may also be enclosed within the housing 302, such as a motor, a motor holder, a thermistor, and an optional lens, for example. Furthermore, in some examples, the catheter tip 26 may include a system for filling the tip with a fluid, such as an acoustic coupling fluid.

The transducer array 306 has several layers stacked along the y-axis and extending along the x-z plane. One or more layers of the transducer array 306 may be layers of transducer elements 312. In one example, the transducer elements 312 may be piezoelectric elements, where each piezoelectric element may be a block formed of a natural material such as quartz, or a synthetic material, such as lead zirconate titanate, that deforms and vibrates when a voltage is applied by, for example, a transmitter. In some examples, the piezoelectric element may be a single crystal with crystallographic axes, such as lithium niobate and PMN-PT ($Pb(Mg_{1/3}Nb_{2/3})O_3$—$PbTiO_3$). The vibration of the piezoelectric element generates an ultrasonic signal formed of ultrasonic waves that are transmitted out of the catheter tip 26. The piezoelectric element may also receive ultrasonic waves, such as ultrasonic waves reflected from a target object, and convert the ultrasonic waves to a voltage. The voltage may be transmitted to a receiver of the imaging system and processed into an image.

An acoustic matching layer 314 may be positioned above the transducer elements 312. The acoustic matching layer 314 may be a material positioned between the transducer elements 312 and a target object to be imaged. By arranging the acoustic matching layer 314 in between, the ultrasonic waves may first pass through the acoustic matching layer 314, and emerge from the acoustic matching layer 314 in phase, thereby reducing a likelihood of reflection at the target object. The acoustic matching layer 314 may shorten a pulse length of the ultrasonic signal, thereby increasing an axial resolution of the signal.

The layers formed by the acoustic matching layer 314 and the transducer elements 312 may be diced along at least one of the y-x plane and the y-z plane to form individual acoustic stacks 316. Each of the acoustic stacks 316 may be electrically insulated from adjacent acoustic stacks 316 but may all be coupled to common layers positioned below or above the transducer elements 312, with respect to the y-axis.

An electrical circuit 318 may be layered below, relative to the y-axis, the transducer elements 312. In one example, the electrical circuit may be at least one application-specific integrated circuit (ASIC) 318 directly in contact with each of the acoustic stacks 316. Each ASIC 318 may be coupled to one or more flex circuits 317 which may extend continuously between the transducer array 306 and the catheter cable 310. The flex circuits 317 may be electrically coupled to the catheter cable 310 to enable transmission of electrical signals between the transducer array 306 and an imaging system, e.g., the imaging system 20 of FIG. 1. The electrical signals may be tuned by the capacitors 308 during transmission.

An acoustic backing layer 320 may be arranged below the ASIC 318, with respect to the z-axis. In some examples, as shown in FIG. 3, the backing layer 320 may be a continuous layer of material that extends along the x-z plane. The backing layer 320 may be configured to absorb and attenuate backscattered waves from the transducer elements 312. A bandwidth of an acoustic signal generated by the transducer elements 312, as well as the axial resolution, may be increased by the backing layer 320.

As described above, the transducer 304, the capacitors 308, and the catheter cable 310 may be enclosed within the housing 302. Thus a size, e.g., a diameter or width of the components may be determined by an inner diameter of the housing 302. An inner diameter of the housing 302 may be, in turn, determined by an outer diameter and a desirable thickness of the housing 302. The outer diameter of the housing 302 may be constrained by a region of a patient's body through which the imaging catheter is inserted. For example, the imaging catheter may be an intracardiac echocardiography (ICE) catheter used to obtain images of cardiac structures and blood flow inside the patient's heart.

The imaging catheter may be introduced into the heart through the aorta, inferior vena cava, or jugular vein. In some instances, the imaging catheter may be fed through regions with narrower diameters, such as the coronary sinus, the tricuspid valve, and the pulmonary artery. As such, the outer diameter of the imaging catheter may not be greater than 10 Fr or 3.33 mm. The outer diameter and corresponding inner diameter of the imaging catheter housing are shown in FIG. 4 in a cross-section 400 of the housing 302 of the catheter tip 26, taken along line A-A' depicted in FIG. 3.

Figure 4:
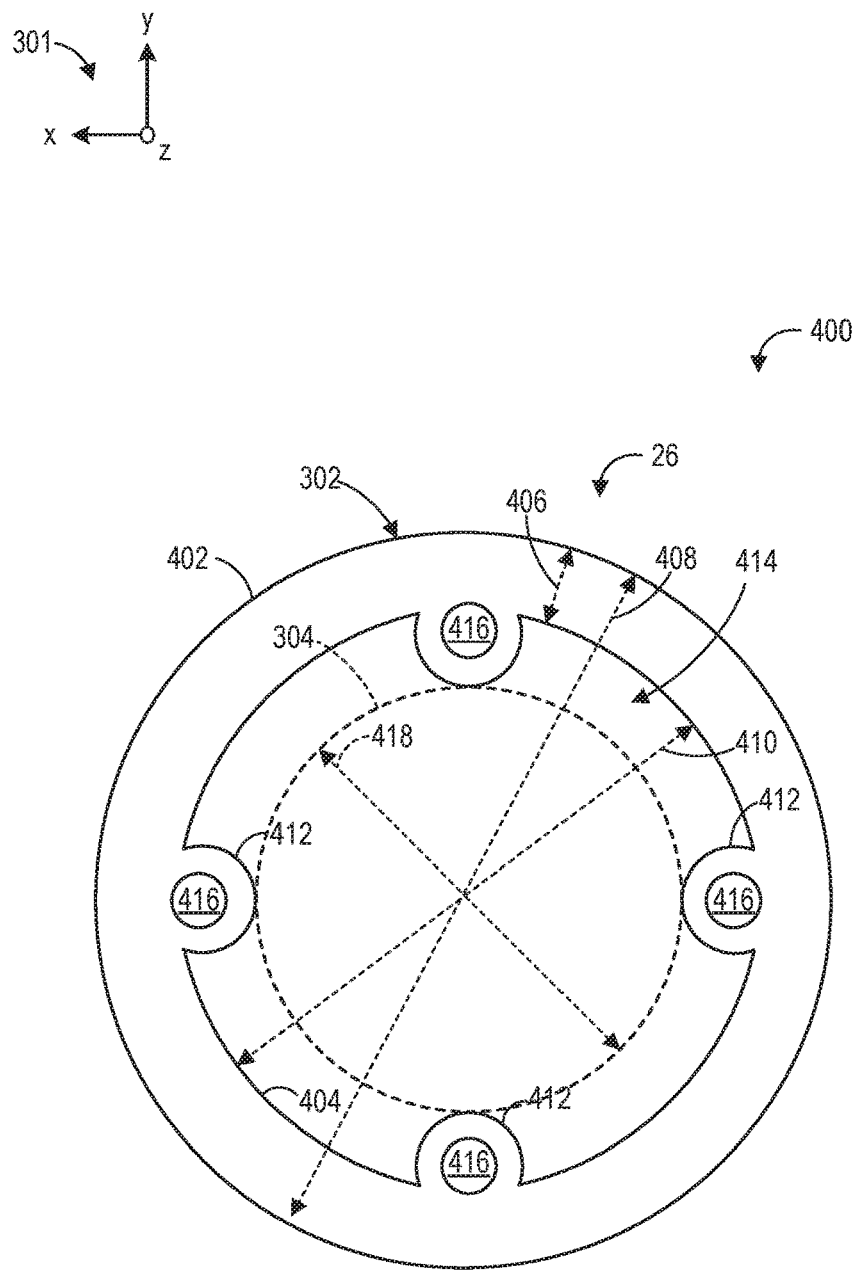
FIG. 4 is a schematic of a cross-sectional view of the deployable catheter of FIG. 2.

As shown in FIG. 4, an outer surface 402 of the housing 302 of the imaging catheter may be spaced away from an inner surface 404 of the housing 302 by a thickness 406 of the housing 302. The thickness 406 of the housing 302 may be optimized to provide the housing 302 with a target degree of structural stability, e.g. resistance to deformation, balanced with flexibility, e.g., ability to bend when a force is applied. In one example, an outer diameter 408 of the housing 302 may be 3.33 mm, the thickness 406 may be 0.71 mm, and an inner diameter 410 of the housing 302 may be 2.62 mm. In other examples, the outer diameter of the housing may be between 2-5 mm, the thickness may be between 0.24-1 mm, and the inner diameter may be between 1-4 mm. In yet other examples, the imaging catheter may have a variety of dimensions, depending on application. For example, an endoscope may have an outer diameter 10-12 mm. It will be appreciated that the imaging catheter may have various diameters and sizes without departing from the scope of the present disclosure.

The inner surface 404 of the housing 302 may include lobes 412 protruding into an inner volume, or lumen 414 of the housing 302. The lobes 412 may be semi-circular projections, each enclosing an individual lumen 416 for housing a steering wire of the imaging catheter. An arrangement of the transducer 304 of the imaging catheter within the lumen 414 of the housing 302 is indicated by a dashed circle. A maximum outer diameter 418 of the transducer 304 may be determined based on a distance between innermost points of oppositely arranged lobes 412. Thus, the outer diameter 418 of the transducer 304 may be smaller than the inner diameter 410 of the housing 302. In some examples, the imaging catheter may not have steering wires and the lobes 412 may be omitted. In such instances the outer diameter 418 of the transducer 304 may be similar to the inner diameter 410 of the housing 302.

The circular geometry of the transducer may pose difficulty during a manufacturing process. For example, laminating acoustic layers in a circular conformation may lead to uneven application of adhesives that may adversely affect transducer performance. Dicing of an acoustic stack in a circular conformation may cause low precision and/or demand use of costly and complex instruments. However, an ease and efficiency of radial transducer fabrication may be enabled by configuring the transducer with a shape memory material. The shape memory material may be a shape memory polymer (SMP) configured to respond mechanically to one or more stimuli. Examples of SMPs include linear block copolymers, such as polyurethanes, polyethylene terephthalate, polyethyleneoxide, and other thermoplastic polymers such as polynorbornene. In one example, the SMP may be a powder mixture of silicone and tungsten in an acrylic resin.

The SMP may be stimulated by physical stimuli, such as temperature, moisture, light, magnetic energy, electricity, etc., by chemical stimuli, such as chemicals, pH level, etc., and by biological stimuli, such as presence of glucose and enzymes. When applied to an imaging catheter, the transducer may incorporate the SMP to enable a shape of the transducer to be altered upon exposure to at least one stimulus. The SMP may have physical properties as provided below in Table 1 which may offer more desirable characteristics than other types of shape memory materials, such as shape memory alloys. For example, SMPs may have a higher capacity for elastic deformation, lower cost, lower density, as well as greater biocompatibility and biodegradability. In particular, the lower cost of SMPs may be desirable for application in disposable deployable catheters.

TABLE 1

Physical Properties of Shape Memory Polymers

| Property | Range |
|---|---|
| Density (g/cm$^3$) | 0.2-3 |
| Extent of deformation | Up to 800% |
| Required stress for deformation (MPa) | 1-3 |
| Stress generated upon recovery (MPa) | 1-3 |
| Transition temperature (° C.) | −10 to 100 |
| Recovery speed | 1 s to 1 hr |
| Processing condition | <200° C.; low pressure |
| Cost | <$10/lb |

In one example, the SMP may have two-way shape memory so that the SMP may adjust between two shapes without demanding reprogramming or application of an external force. For example, the SMP may convert to a temporary shape in response to a first stimulus and revert to a permanent shape in response to a second stimulus. The first and second stimuli may be of a same or different type of stimulus, e.g., the first stimulus may be a high temperature and the second stimulus may be a low temperature or the first stimulus may be a humidity level and the second stimulus may be a threshold temperature. The two-way shape memory behavior is neither mechanically nor structurally constrained, thereby allowing the SMP to switch between the temporary shape and permanent shape without applying the external force. In this way, the SMP may be adjusted to a conformation more favorable for assembling a radial transducer and returned to a radial geometry for deployment.

Figure 14:
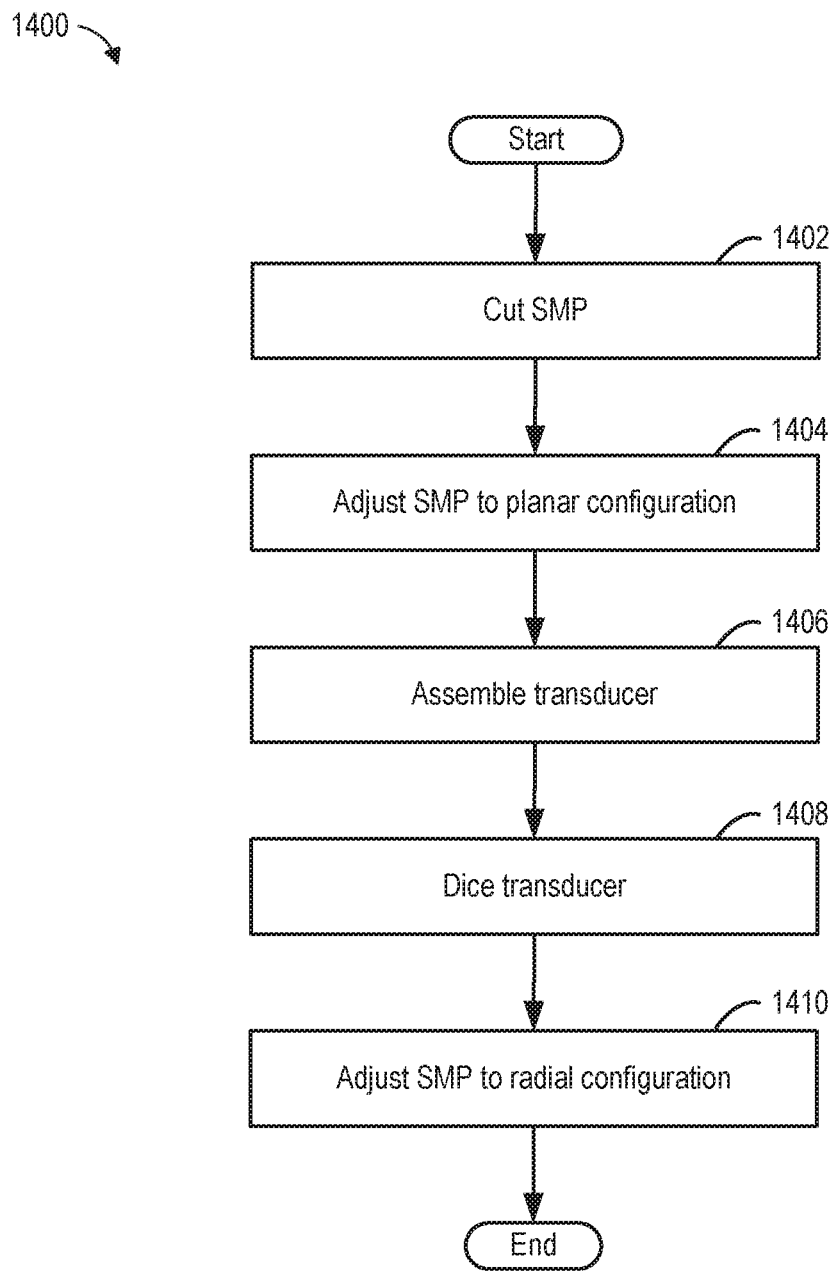
FIG. 14 is an example of a method for fabricating a radial transducer adapted with a SMP.

As an example, manufacturing of a radial transducer is shown in FIG. 14 in an example of a method 1400 for fabricating the transducer. The method 1400 may be implemented by one or more machines, such as machines configured for dicing and/or grinding. The machines may include instructions stored in memory executable by a process or to implement the different steps. To elaborate, at least some of the method steps may be implemented as an automated machine process. However, in other examples, at least some of the steps may be implemented in response to user input or may be manually implemented via manufacturing personnel. The manufacturing process is further illustrated in a first diagram 500 in FIG. 5.

At 1402, the method includes cutting a SMP to a desired geometry. The SMP may be in a circular configuration which may be a permanent configuration of the SMP. As an example, at a first step 501 of the diagram 500 of FIG. 5, the SMP 502 is in a continuous circular configuration. The SMP 502 may be a block of a rigid two-way shape memory material provided as, for example, a tube with a thickness (e.g., a difference between an outer diameter and an inner diameter of the tube) of between 200 μm to 5 mm. The tube may be sliced into desired sections, e.g., cut along the z-axis into segments conforming to a desired azimuth aperture of a transducer. The SMP 502 is diced at a second step 503 to form a gap 504 in the SMP 502 so that the SMP 502 is no longer continuous. The gap 504 may be, for example, between 20-40 μm wide.

Returning to FIG. 14, at 1404, the method includes adjusting the SMP to a planar configuration. For example, as shown in FIG. 5, the SMP 502 may be programmed to transition to a second, temporary shape at a third step 505 of the diagram 500 upon exposure of the SMP 502 to a first stimulus, $S_1$. The first stimulus $S_1$ may be a straightening stimulus, e.g., causes the SMP 502 to straighten, and may be a variety of stimuli, including humidity, temperature, UV light, etc. In response to the first stimulus $S_1$, the SMP 502 may become planar, e.g., parallel and aligned with the x-z plane.

A transition behavior of the SMP 502 when exposed to the first stimulus $S_1$ may include the SMP 502 converting from the rigid material to a pliable one and automatically becoming flat once sufficiently pliable, for example. When converted to the planar configuration shown at the third step 505, the SMP 502 may return to the original rigidity. The SMP 502 may be ground, while in the planar configuration, to a desired thickness, such as 700 μm, for example. In other examples, the thickness of the SMP 502 may be between 200 μm to 5 mm. Grinding of the SMP 502 may also adjust a texture, e.g., a roughness of surfaces of the SMP 502.

At 1406 of method 1400 shown in FIG. 14, a transducer may be assembled by coupling an acoustic stack to the SMP. For example, as shown at a fourth step 507 in FIG. 5, an acoustic stack 506, including a backing layer, a flexible printed circuit board, one or more piezoelectric ceramic layers, and a matching layer, may be laminated to one face of the SMP 502. Laminating the acoustic stack 506 onto the SMP 502 forms a transducer 508 which may be implemented in a deployable catheter.

The transducer is cut or diced at 1408 of FIG. 14. For example, as shown at a fifth step 509 in FIG. 5, dicing the acoustic stack 506 forms a plurality of kerfs 510 extending through the acoustic stack 506 along the y-axis which divides the acoustic stack 506 into individual transducer elements 512. The acoustic stack 506 may be diced via various techniques, including scribing and breaking, mechanical sawing, or laser cutting, for example. Variations in dicing of the transducer is described further below, with reference to FIGS. 6-7 and 15, resulting in different kerf configurations. As such, the transducer 508 may include at least one array of transducer elements 512.

Turning again to FIG. 14, at 1410, the method includes returning the SMP to the radial, e.g., circular, configuration. The method then ends. For example, at a sixth step 511 in FIG. 5, the transducer 508 is exposed to a second stimulus $S_2$. The second stimulus may be a curling stimulus, e.g., causing the SMP to curl or bend. In response to the second stimulus $S_2$, the SMP 502 returns to the permanent, circular configuration. The transducer elements 512 may be located along an outer surface of the SMP 502 in the circular configuration, e.g., the transducer elements 512 face outwards. Thus, the transducer 508 may have a 360° FOV when adjusted to the permanent configuration.

The transition behavior of the SMP 502 when exposed to the second stimulus $S_2$ may include softening of the SMP 502 to become more pliable. Upon softening, the planar SMP 502 may automatically curl and return to the circular configuration. In the circular configuration, the SMP 502 may return to the rigid state.

The second stimulus $S_2$ may be of a same or different type as the first stimulus $S_1$. For example, the first and second stimuli $S_1$, $S_2$ may both be temperatures, with the first stimulus $S_1$ a higher temperature than the second stimulus $S_2$. Alternatively, as another example, the first stimulus $S_1$ may be a temperature value higher than ambient temperature and the second stimulus $S_2$ may be an elevated humidity level relative to ambient humidity. The stimuli thresholds may be selected based on anticipated conditions when the deployable catheter is inserted into a patient. As one example, the first stimulus $S_1$, if based on temperature, may be a higher temperature than an internal temperature of the patient to circumvent transitioning of the transducer to the planar configuration during deployment in the patient for data acquisition, such as imaging. As another example, a stimulus that the transducer will not be exposed to within the patient may be used to convert the SMP between geometries, such as UV light or a chemical stimulus. In another example, the shape of the SMP may be maintained using mechanical restraints. The stimuli may be a type of physical stimulus that is readily controlled in a manufacturing environment, such as temperature, humidity, or UV light. However, the stimuli may be variety of types, including chemical, biological and physical stimuli.

As described above, dicing of the transducer divides the transducer into transducer elements. By enabling the dicing to be performed with the transducer in the planar configuration, dicing of the acoustic stack may be tuned to a desired kerf depth. For example, as shown in FIG. 6, a first diced example 600 of the transducer 508 of FIG. 5 may include the plurality of kerfs 510 extending through a portion of a height 602 of the acoustic stack 506 of the transducer 508.

The acoustic stack 506 may be formed of acoustic layers, including, from a top of the acoustic stack 506 to a bottom, relative to the y-axis, a matching layer 604, one or more piezoelectric crystals 606, a flexible electrical circuit (hereafter, flex) 608, and a backing layer 610. The acoustic layers may be similar to those described above with respect to FIG. 3 and may be coupled to one another and to the SMP 502 via conventional methods such as stack lamination, coating, etc. In the first diced example 600, a depth 612 of each of the plurality of kerfs 510 is less than the height 602 of the acoustic stack 506. More specifically, the depth 612 of the plurality of kerfs 510 extends from the top of the acoustic stack 506 into the backing layer 610 but not entirely through the backing layer 610.

In contrast, in a second diced example 700 of the transducer 508, the plurality of kerfs may have a different depth 702 than the depth 612 of the plurality of kerfs 510 shown in FIG. 6. The depth 702 of the plurality of kerfs 510 of the second diced example 700 is greater than the height 602 of the acoustic stack 506. More specifically, the plurality of kerfs 510 extend from the top of the acoustic stack 506 through a bottom of the backing layer 610 and into a portion of a thickness 704 of the SMP 502.

Figure 15:
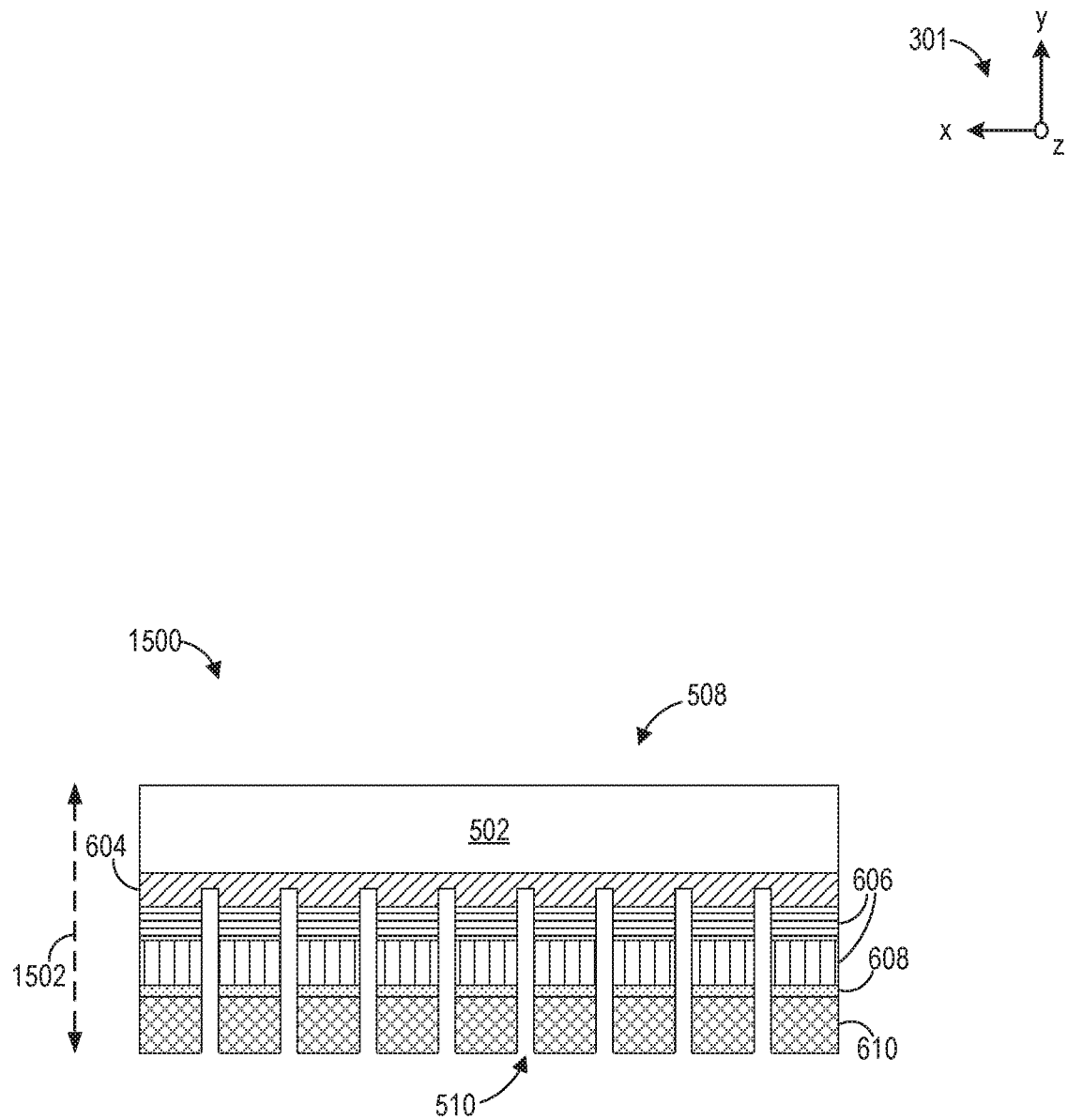
FIG. 15 shows a third example of how a transducer adapted with a shape memory material may be diced.

While the transducer 508 shown in FIGS. 5-7 is depicted with the SMP 502 coupled to and in face-sharing contact with an outward-facing surface (e.g., bottom face, with respect to the y-axis) of the backing layer 610, in other examples, the SMP 502 may be positioned at an opposite side of the transducer 508. For example, as shown in FIG. 15, the SMP may instead be coupled to and in face-sharing contact with an outward-facing (e.g., top face) surface of the matching layer 604. In such instances, the plurality of kerfs 510 may extend upwards from the bottom face of the backing layer 610 through a portion of a height 1502 of the transducer 508.

By varying the depth of the plurality of kerfs 510, sharing of acoustic layers between the transducer elements 512 may be controlled. For example, in the first diced example 600 of FIG. 6, the backing layer 610 is maintained as a continuous, common layer in electrical communication with each of the transducer elements 512. In the second diced example of FIG. 7, however, each transducer element 512 is electrically insulated from one another by extension of the plurality kerfs 510 entirely through the height 602 of the acoustic stack 506. Thus, an electrical configuration of the transducer may be adjusted by dicing of the transducer and may be readily controlled when the transducer is in a planar, flat configuration. In contrast, dicing the transducer when the transducer is in a circular configuration may lead to imprecise dicing, degrading transducer performance.

It will be appreciated that the examples of dicing of the transducer shown in FIGS. 6 and 7 are non-limiting examples. Other examples may include differences in the depth of the plurality of kerfs from those shown, non-uniform depths amongst the plurality of kerfs, as well as non-uniform spacing of the plurality of kerfs.

An SMP may be implemented in a transducer as a structural component (e.g., as shown in FIGS. 5-7, serving as a backing substrate to which an acoustic stack is coupled, thereby varying a shape of the transducer when the SMP transitions from one geometry to another. In some examples, however, the SMP may positioned between acoustic layers rather than as a terminal layer, e.g., arranged along a top or a bottom of an acoustic stack. Furthermore, in other examples, the SMP may be configured as an acoustic layer of the transducer and actively involved in operation of a transducer probe. Examples of transducers showing variations in placement and implementation of a SMP are shown in FIGS. 9-11. The transducers are shown without dicing for brevity but may be diced as shown in FIGS. 6-7 and 15 or other configurations.

As shown in FIG. 8, a first arrangement of a transducer 800, as an alternative to the arrangement shown in FIGS. 5-7, may include, from a top of the transducer 800 to a bottom with respect to the y-axis, a matching layer 802, one or more piezoelectric crystals 804, a flex 806, a SMP 808, and a backing layer 810. The SMP 808 is arranged as a layer between the flex 806 and the backing layer 810 so that the flex 806 may be coupled to a top face of the SMP 808 and the backing layer 810 may be coupled to a bottom face of the SMP 808. In this configuration, the SMP 808 may be formed from a material that is transparent to data transmission sources. For example, in an ultrasound probe, the SMP 808 may be a material that does not affect transmission of ultrasound waves and is electrically conductive. As such, the SMP 808 does not affect signal transmission and data acquisition. Furthermore, other examples may include the SMP 808 arranged between any of the layers of the transducer 800, e.g., between the flex 806 and one of the piezoelectric crystals 804, between one of the piezoelectric crystals 804 and the matching layer 802. In yet another example, the backing layer 810 may be arranged between one or more piezoelectric crystals 804 and the flex 806 and the SMP 808 may be positioned below and directly coupled to the flex 806.

Alternatively, as shown in FIG. 9 in a second arrangement of a transducer 900, a SMP 902 may be configured as a backing layer of the transducer 900. The SMP 902 may be in face-sharing contact with the flex 806 and coupled to a bottom face of the flex 806. When implemented as the backing layer of the transducer 900, the SMP 902 may be formed from a material tuned to maximize attenuation at a desired frequency. For example, higher density loads such as tungsten powder, epoxy powder, silicone powder, etc., may be added to a polymeric matrix of the SMP 902 to increase an attenuative property of the SMP material.

In a third arrangement of a transducer 1000, as shown in FIG. 10, a SMP 1002 may be configured as a matching layer of the transducer 1000. The SMP 1002 may form a top layer of the transducer 1000, in face-sharing contact and coupled to a top face of one of the piezoelectric crystals 804. When implemented as the matching layer of the transducer 1000, a material of the SMP 1002 may already have acoustically impeding properties but an acoustic impedance of the SMP 1002 may be adjusted by adding higher density loads, such as tungsten powder epoxy powder, silicone powder, etc.

By enabling a radial transducer to be assembled while in a planar configuration, a positioning of a SMP in the transducer may be adjusted according to a desired application. The positioning of the SMP may be varied without demanding use of additional, more complex tooling and the SMP may be implemented as an acoustic layer, thereby reducing a number of layers in the transducer and simplifying fabrication. High precision fabrication of the transducer is enabled in each configuration, thereby maintaining a performance of the transducer.

As described previously, in one example, a radial transducer may have a 360° FOV desirable for applications such as endoscopic ultrasound imaging, breast imaging, etc. In addition, other conformations of the radial transducer may be formed by the process described above with reference to FIGS. 5-10. For example, a radial transducer with a less than 360° may be manufactured with a SMP as a structural backing and/or as an acoustic layer to control a shape of the transducer during fabrication. The radial transducer may be a convex or concave transducer, as shown in FIGS. 11-12.

An example of a convex transducer 1100 is illustrated in FIG. 11. The convex transducer 1100 has a semi-circular geometry, e.g., half of a circle, and a signal transmission direction is indicated by arrows 1102. However, if a SMP 1104 is used as a matching layer of the convex transducer 110, the signal transmission direction may opposite of that indicated by arrows 1102. The SMP 1104 may form an innermost layer of the convex transducer 1100. In other words, the SMP 1104 may be closer to a central axis of rotation 1106 and further from a scanning target (e.g., a target region from which data is to be collected) of the convex transducer 1100 than an acoustic stack 1108 of the convex transducer 1100. The acoustic stack 1108 may form outer layers of the convex transducers and provide a 180° FOV. The convex transducer may be implemented in, for example, endoscopes and laparoscopes.

An example of a concave transducer 1200 is depicted in FIG. 12. The concave transducer 1200 also has a semi-circular geometry and a signal transmission direction is indicated by arrows 1202. A SMP 1204 may form an outer most layer of the concave transducer 1200. In other words, the SMP 1204 may be further from a central axis of rotation 1206 of the concave transducer 1200 1106 and further from a scanning target than an acoustic stack 1208 of the concave transducer 1200. The concave transducer 1200 may have a narrower, focused FOV than the convex transducer 1100 of FIG. 11, and may be used for applications such as high-intensity focused ultrasound (HIFU).

Other examples of radial transducers incorporating a SMP to adjust the transducers to a planar configuration during fabrication may include transducers forming various portions of a circle. For example, a radial transducer may form a quarter-circle, three-quarters of a circle, in either of a concave or convex configuration. The radial transducer may have a FOV anywhere between 10-360°.

The manufacturing process for a radial transducer described herein may be further applied to fabrication of non-radial transducers, such as a linear array transducer. For example, a transducer may be configured with a SMP to adjust a size and shape of the transducer between a first conformation that is more favorable for intravenous passage of the transducer, when implemented in a deployable catheter, and a second conformation that increases an active area of the transducer to enhance a performance of the transducer.

Figure 13:
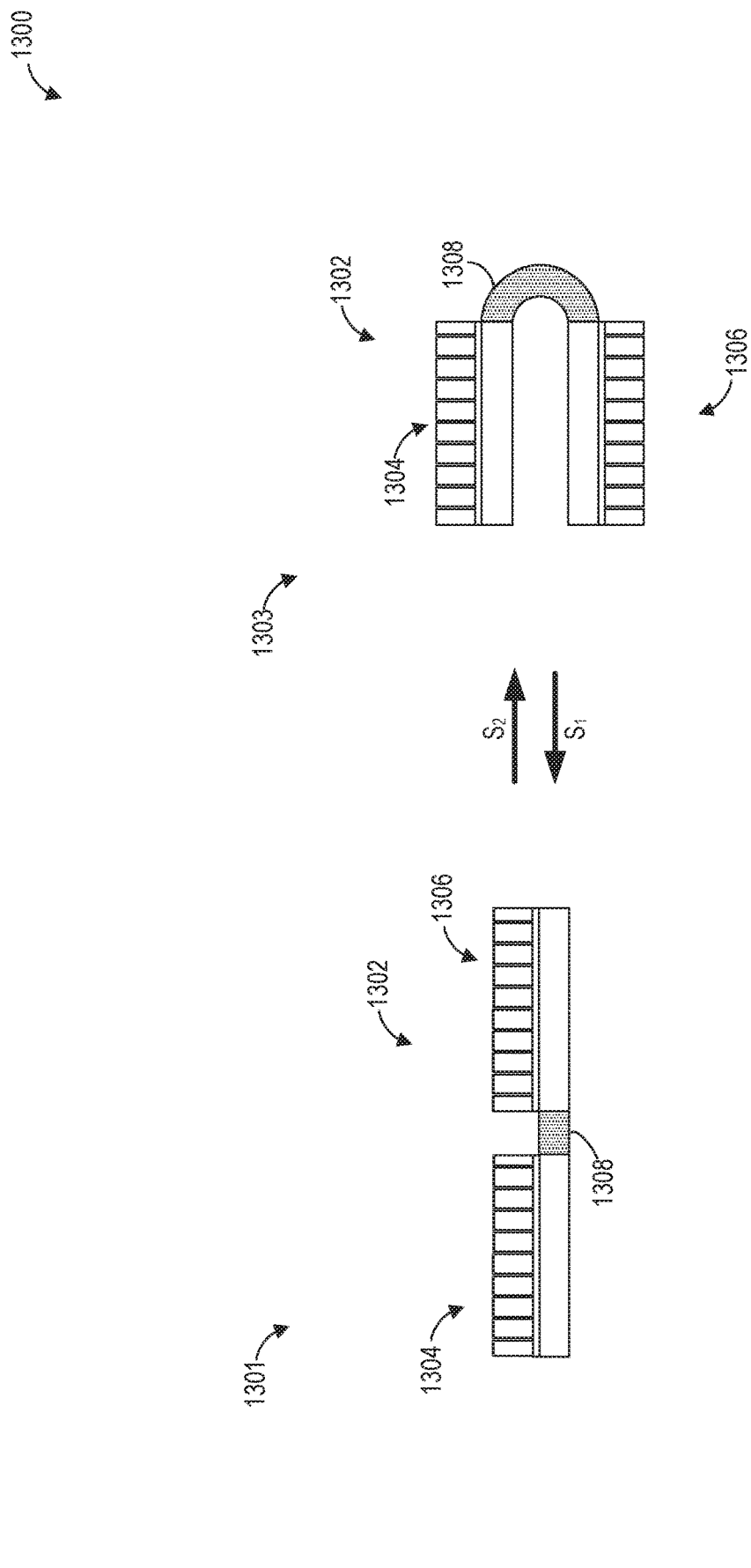
FIG. 13 is a second diagram showing a transition of a transducer adapted with a SMP to an alternative configuration.

As an example, conversion of a transducer 1302 between a first shape 1301 and a second shape 1303 is shown in a diagram 1300 in FIG. 13, where the second shape 1303 may be a folded shape. The transducer 1302 includes a first transducer array 1304 and a second transducer array 1306 linked by a SMP 1308. The SMP 1308 may be incorporated into the transducer 1302 in a variety of configurations. For example, the SMP 1308 may be a section of shape memory material extending between the first and second transducer arrays 1304, 1306 and coupled to inner edges of the transducer arrays. Alternatively, the SMP 1308 may form an acoustic layer of the transducer 1302, such as a backing layer or a matching layer. As yet another example, the SMP 1308 may be attached to one side of the transducer 1302 along edges of each of the transducer areas and positioned outside of an active area of the transducer 1302 where the active area is defined as a total surface area of the transducer arrays facing a same direction.

Regardless of a positioning of the SMP 1308, the SMP 1308 may be adjusted to a planar configuration to enable assembly and dicing of the transducer 1302. For example, the SMP 1308 may be provided in a permanent conformation as a tube, as shown in FIG. 5 and may be cut according to a desired shape of the SMP 1308. As an example, the tube may be sliced in half so that the SMP 1308 has a semi-circular configuration. The SMP 1308 may be exposed to a first stimulus $S_1$, as described above with reference to FIG. 5, to adjust the SMP 1308 to the planar configuration. In the planar configuration, the transducer 1302 may be assembled and diced which may include coupling the SMP 1308 to one or more components of an acoustic stack, e.g., to edges of the backing layer or matching layer, and/or laminating the acoustic stack onto the SMP 1308, etc. The assembled transducer 1302 may be in the first shape 1301.

When the transducer 1302 is assembled, the transducer 1302 may be exposed to a second stimulus $S_2$, which may be of a same or different type as the first stimulus $S_1$. Exposure to the second stimulus may induce transitioning of the SMP 1308 to the permanent, semi-circular shape which adjusts the transducer 1302 to the second, folded shape 1303. In the second shape 1303, the active area of the transducer 1302 is reduced and a footprint of the transducer is decreased, allowing the transducer 1302 to be inserted through narrow passages, such as arteries or veins of a patient. When the transducer 1302 is deployed and reaches a target site, the transducer 1302 may be exposed to the first stimulus $S_1$ to adjust the transducer 1302 to the first shape 1301, thereby increasing the active area. As such, a resolution, penetration, and data acquisition speed of the transducer 1302 may be increased.

It will be appreciated that the folded conformation of the transducer shown in FIG. 13 is a non-limiting example of how the footprint of the transducer may be reduced. Other examples may include other manners of shape change other than bending or folding. For example, the SMP may curl into a jellyroll configuration and/or shrink along at least one dimension.

In this way, a radial transducer may be fabricated with increased precision without use of complex tooling. The transducer may include a SMP, either as an inert layer or as incorporated as an acoustic layer, to adjust a geometry of the transducer in response to one or more stimuli. The transducer may thereby be in a planar configuration during assembly of the transducer and returned to a radial conformation when coupling of an acoustic stack to the SMP and dicing of the stack are complete. As a result, a production yield of the manufacturing process may be increased while enabling modification of an arrangement of the transducer with high precision and consistency and at low cost.

The technical effect of adapting a radial transducer with a shape memory material is that high precision fabrication of the radial transducer is simplified.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The disclosure also provides support for a method for forming a transducer, comprising: coupling an acoustic stack to a shape memory material while in a planar configuration to form a transducer, and exposing the shape memory material to a curling stimulus to adjust the transducer to a curved configuration. In a first example of the method, the method further comprises: prior to coupling the acoustic stack to the shape memory material, exposing the shape memory material to a straightening stimulus to transition the shape memory material from the curved conformation to the planar configuration. In a second example of the method, optionally including the first example, exposing the shape memory material to the straightening stimulus includes exposing the shape memory material to at least one of a physical, chemical, or biological stimulus. In a third example of the method, optionally including the first and second examples, exposing the shape memory material to the curling stimulus includes exposing the shape memory material to the curling stimulus to activate curling of the shape memory material after the shape memory material is exposed to the straightening stimulus and in the planar configuration. In a fourth example of the method, optionally including the first through third examples, exposing the shape memory material to the curling stimulus includes exposing the shape memory material to a stimulus that is a same or different type as the straightening stimulus. In a fifth example of the method, optionally including the first through fourth examples, a threshold of the straightening stimulus, above which straightening of the shape memory material is activated, is above a range of the straightening stimulus imposed on the shape memory material upon insertion into a patient during data acquisition by the transducer. In a sixth example of the method, optionally including the first through fifth examples, transitioning the shape memory material from the curved configuration to the planar configuration includes decreasing a rigidity of the shape memory material to enable transition from the curved configuration to the planar configuration and restoring the rigidity of the shape memory material when in the planar configuration and wherein returning the shape memory material from the planar configuration to the curved configuration includes decreasing a rigidity of the shape memory material to enable curling of the shape memory material and restoring the rigidity of the shape memory material when in the curved configuration. In a seventh example of the method, optionally including the first through sixth examples, coupling the acoustic stack to the shape memory material includes laminating at least one of a backing material, a flexible electrical circuit, a piezoelectric crystal, and a matching layer to a surface of the shape memory material. In an eighth example of the method, optionally including the first through seventh examples, forming the transducer includes dicing a plurality of kerfs into the transducer while the shape memory material is in the planar configuration. In a ninth example of the method, optionally including the first through eighth examples, forming the transducer includes forming one of a matching layer and a backing layer from the shape memory material.

The disclosure also provides support for a transducer for a deployable catheter, comprising: an acoustic stack coupled to a shape memory polymer, the shape memory polymer configured to transition between a first configuration and a second configuration in response to one or more stimuli. In a first example of the system, the first configuration is any of a folded, convex, concave, spiral, and circular geometry and where in the second configuration is planar. In a second example of the system, optionally including the first example, the system further comprises: a plurality of kerfs diced into the transducer and wherein the plurality of kerfs extend into a portion of a height of the transducer. In a third example of the system, optionally including the first and second examples, the shape memory polymer is coupled to an outward-facing surface of one of a backing layer and a matching layer of the transducer. In a fourth example of the system, optionally including the first through third examples, the shape memory polymer is one of a backing layer or matching layer of the transducer. In a fifth example of the system, optionally including the first through fourth examples, the shape memory polymer is positioned between any layers of the transducer. In a sixth example of the system, optionally including the first through fifth examples, the transducer is a radial transducer with a field of view up to 360°.

The disclosure also provides support for a method for fabricating a transducer, comprising: adjusting a shape memory polymer (SMP) to a non-radial configuration, laminating transducer components to the SMP while in the non-radial configuration, dicing the transducer components, and adjusting the SMP to a radial configuration to form the transducer with a wide field of view. In a first example of the method, adjusting the SMP to the radial configuration includes adjusting the transducer to any of a circular, folded, spiral, convex, and concave conformation. In a second example of the method, optionally including the first example, adjusting the SMP to the radial configuration includes transitioning the transducer to a geometry with a radius of curvature enabling the transducer to be enclosed within a deployable catheter.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for forming a transducer, comprising:
forming a shape memory polymer (SMP) from a powder mixture of silicon and tungsten that is mixed into a matrix of an acrylic resin;
exposing the SMP to a straightening stimulus to adjust the SMP to a planar configuration;
coupling a first acoustic stack and a second acoustic stack to opposites ends of the SMP, while in the planar configuration to form the transducer; and
exposing the SMP to a curling stimulus to adjust the SMP to a curved configuration and the transducer to a folded configuration;
wherein the straightening stimulus includes a physical stimulus or a chemical stimulus;
wherein the curling stimulus is a stimulus that the transducer is not exposed to within a patient; and
wherein the straightening stimulus is of a different type than the curling stimulus.

2. The method of claim 1, wherein the planar configuration is a temporary configuration and the curved configuration is a permanent configuration of the SMP.

3. The method of claim 1, wherein acoustic properties of the SMP are varied according to a loading of the powder mixture of silicone and tungsten, and wherein the acoustic properties include acoustic attenuation and acoustic impedance.

4. The method of claim 1, wherein a threshold of the straightening stimulus, above which straightening of the SMP is activated, is above a range of the straightening stimulus imposed on the SMP upon insertion into a patient during data acquisition by the transducer.

5. The method of claim 1, wherein transitioning the SMP from the curved configuration to the planar configuration includes decreasing a rigidity of the SMP to enable transition from the curved configuration to the planar configuration and restoring the rigidity of the SMP when in the planar configuration, and wherein returning the SMP from the planar configuration to the curved configuration includes decreasing the rigidity of the SMP to enable curling of the SMP and restoring the rigidity of the SMP when in the curved configuration.

6. The method of claim 1, wherein forming the transducer includes dicing a plurality of kerfs into the transducer while the SMP is in the planar configuration.

7. The method of claim 1, wherein the physical stimulus includes at least one of temperature, moisture, light, magnetic energy, or electricity.

8. The method of claim 1, wherein the chemical stimulus includes at least one of chemicals or pH level.

9. A transducer for a deployable catheter, comprising:
an acoustic stack coupled to a shape memory polymer (SMP), the SMP configured to transition between a first configuration in response to a first stimulus and a second configuration in response to a second stimulus, the second stimulus being of a different type than the first stimulus, wherein the first stimulus includes a physical stimulus or a chemical stimulus, wherein the second stimulus is a stimulus that the transducer is not exposed to within a patient, and wherein the SMP is formed of a powder mixture of silicone and tungsten that is mixed into a matrix of an acrylic resin,
wherein the acoustic stack is divided into a first array and a second array and the SMP is arranged between the first array and the second array, each of opposite ends of the SMP being coupled to an inner edge of the first array and the second array, respectively.

10. The transducer of claim 9, wherein the first configuration is any of a folded, convex, concave, spiral, and circular geometry, and wherein the second configuration is planar.

11. The transducer of claim 9, wherein the powder mixture of silicone and tungsten is mixed into a matrix of an acrylic resin.

12. The transducer of claim 10, further comprising a plurality of kerfs diced into the transducer while the SMP is planar.

13. The transducer of claim 9, wherein the transducer has a plurality of layers including one or more of transducer elements, a matching layer, an electrical circuit, and a backing layer.

14. The transducer of claim 9, wherein the transducer is a radial transducer with a field of view up to 360°.

15. A method for fabricating a transducer, comprising:
adjusting a shape memory polymer (SMP) to a planar configuration by exposing the SMP to a first stimulus, wherein the first stimulus includes a physical stimulus or a chemical stimulus;
laminating transducer components to the SMP while in the planar configuration;
dicing the transducer components; and
adjusting the SMP to a curved configuration by exposing the SMP to a second stimulus to form the transducer with a wide field of view, wherein the second stimulus is a stimulus that the transducer is not exposed to within a patient, and wherein the second stimulus is different from the first stimulus,
wherein the transducer is divided into a first array and a second array, and the SMP is arranged between the first array and the second array, each of opposite ends of the SMP being coupled to an inner edge of the first array and the second array, respectively, and
wherein the SMP is formed of a powder mixture of silicone and tungsten that is mixed into a matrix of an acrylic resin.

16. The method of claim 15, wherein adjusting the SMP to the curved configuration includes adjusting the SMP to any of a circular, folded, spiral, convex, and concave conformation.

17. The method of claim 15, wherein adjusting the SMP to the curved configuration includes transitioning the transducer to a geometry with a folded configuration enabling the transducer to be enclosed within a deployable catheter.

* * * * *